United States Patent [19]
Josephberg

[11] Patent Number: 5,716,363
[45] Date of Patent: Feb. 10, 1998

[54] PARS PLANA VITRECTOMY TOOL

[76] Inventor: Robert Gary Josephberg, 11 Tanglewood Cir., Briarcliff Manor, N.Y. 10510

[21] Appl. No.: 632,552

[22] Filed: Apr. 15, 1996

[51] Int. Cl.[6] ........................................ A61F 9/00
[52] U.S. Cl. .................. 606/107; 606/166; 606/171; 604/22
[58] Field of Search .................. 604/19, 22, 27, 604/35; 606/1, 107, 166–185

[56] References Cited

U.S. PATENT DOCUMENTS

| | | | |
|---|---|---|---|
| 5,047,008 | 9/1991 | Juan et al. | 604/22 |
| 5,364,405 | 11/1994 | Zaleski | 604/22 |

OTHER PUBLICATIONS

Dutch Ophthalmic Price List 1992.
Howard Instruments Catalog 1993.
Visitec Catalog and Price List 1992.
Visitec Catalog 1995.
Jaffe, Glenn J. Seminars in Ophthamology/Diagnostic Vitrectomy in the Management of Ocular Disease pp. 15–23.
Visitec Products Catalog 1996.
Sabbagh, Leslie Ophthalmology Times Weekly/Vitreoretinal Surgery–In–Office Vitrectomy Made Easy 1996.

*Primary Examiner*—Glenn Dawson
*Attorney, Agent, or Firm*—Brett J. Trout

[57] ABSTRACT

An intracellular surgical tool for removing material from an eye of a patient. The tool is provided with a blade to allow the tool to make its own incision in the eye. The tool is provided with a cutting assembly and an aspiration apparatus to remove a portion of vitreous from the eye for inspection and testing. The tool is also fitted with a mechanism for replacing the removed vitreous with saline or similar fluid. The tool is portable having a housing and battery pack releasably coupled to one another. The cutting assembly is releasably secured to the housing. Accordingly, the housing may be removed and the cutting assembly discarded so that the housing may be sterilized before performing a vitrectomy.

21 Claims, 3 Drawing Sheets

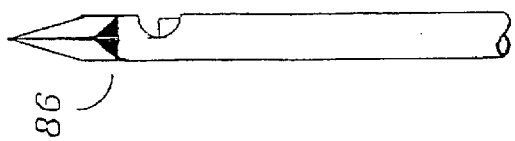
Fig. 5a
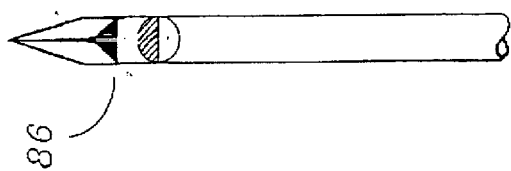
Fig. 5b
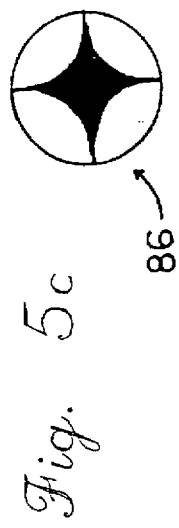
Fig. 5c
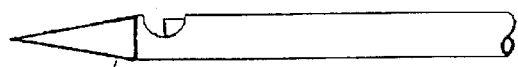
Fig. 4a
Fig. 4b
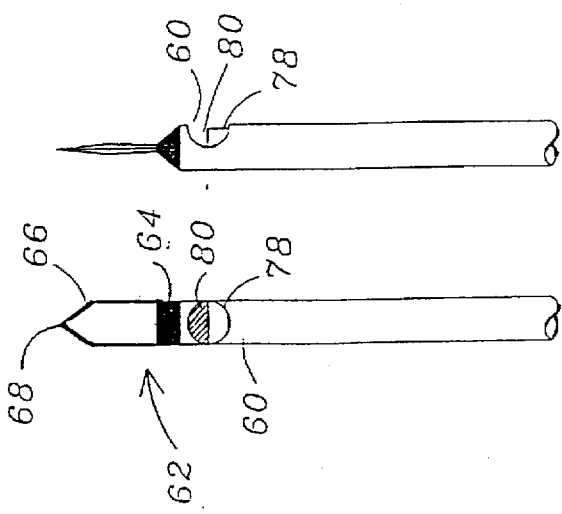
Fig. 3a
Fig. 3b

PARS PLANA VITRECTOMY TOOL

BACKGROUND OF THE INVENTION

Field of the Invention

The present invention relates to a vitrectomy tool and, more particularly, to a vitrectomy cutter provided with a bladed tip allowing the tool to make its own incision for performing a vitrectomy of the eye.

Vitreous inflammatory diseases are often associated with a poor prognosis for the patient. Accurate diagnosis and early treatment of endophthalmitis and other acute forms of vitritis is essential. Traditionally, two options have been available for managing a patient with endophthalmitis. The first option is a vitreous tap which may be performed in a doctor's office or operating room. The second option is a pars plana vitrectomy which, due to the required equipment and complexity of the operation, is performed in an operating room.

While vitreous taps may be safely performed in an office setting, as well as in the operating room, many times it is difficult to aspirate liquid vitreous. This is due to the density of the vitreous cavity and the gauge of the needle (eighteen to twenty gauge) required to aspirate the vitreous. The vitreous tap has the advantage of rapid diagnosis and treatment. The major disadvantages of the vitreous tap include, but are not limited to, vitreous traction, retinal tears and/or retinal detachments.

Pars plana vitrectomy can overcome some of the problems associated with vitreous tap. Pars plana vitrectomy provides a larger vitreous sample for analysis, which may increase the diagnostic yield of organisms. It also may facilitate intracellular antibiotic penetration and allow better clearance of the toxins. The major disadvantage of the pars plana vitrectomy is that it is traditionally performed in an operating room. Operating room scheduling, rooms set-up, equipment set-up and patient admitting and testing may cause delays. Since time is of the essence with endophthalmitis, any delays in diagnosis and treatment can have devastating effects. Additionally, pars plana vitrectomy is a more difficult procedure involving several steps, and is associated with the possibility of more complications, than the vitreous tap.

Pars plana vitrectomy involves a four step procedure. First a sclerotomy is made in the eye with a stiletto knife or similar tool. Second, a reciprocating cutter device is inserted through the sclerotomy to remove a portion of vitreous from the eye. As slices of vitreous are cut from the eye, they are aspirated into a sample collection container for subsequent diagnosis. The cutter is then removed from the eye. Third, saline or similar fluid is injected into the eye through the sclerotomy. Fourth, once the eye has been returned to its initial volume, the sclerotomy is sutured closed. Suturing typically involves additional problems such as increased time in the operating room and increased cost for the sutures. Sutures also increase the possibility of infection in and along the suture tract.

Although prior art patents such as U.S. Pat. No. 4,314,560 teach a raked point on the end of a vitrectomy instrument, such points merely facilitate penetration of the vitrectomy instrument through a sclerotomy previously provided in the eye. Accordingly, while prior art pointed tips may facilitate insertion of a vitrectomy instrument, there is no teaching which would allow elimination of the pre-vitrectomy sclerotomy with a separate blade.

Although the above-described techniques are adapted to provide a vitreous sample for testing, as noted above, both the vitreous tap and the pars plana vitrectomy have drawbacks for the patient. The difficulties encountered hereinabove are sought to be eliminated by the present invention.

SUMMARY OF THE INVENTION

The present invention comprises an intraocular surgical tool for removing material from an eye of a patient. The tool is provided with a housing having a proximal end and a distal end. A cutter assembly is secured to the proximal end of the housing. The cutter assembly includes an outer cutter which has a sidewall defining a longitudinal bore, the longitudinal bore being provided with an aperture. Means, preferably a surgical blade, are secured to the outer cutter for incising a sclerotomy in the eye. The surgical blade is preferably constructed for incising a small enough sclerotomy to heal without sutures, but large enough to accommodate the outer cutter. The tool also includes an inner cutter, which has a cutting edge and which is telescopically received in the longitudinal bore of the outer cutter. The inner cutter is adapted for travel across a cutting edge of the aperture. A linear actuator is provided in the housing and drivably coupled to the inner cutter. The tool is also provided with means releasably coupled to the linear actuator for powering the linear actuator.

In the preferred embodiment of the present invention the cutter assembly is releasably secured to the housing and may be disposable or non-disposable. The tool is also preferably provided with a solenoid actuator or similar varying means to vary the cycling speed of the linear actuator. The tool may be provided with means in operable communication with the longitudinal bore for providing suction to the longitudinal bore.

The method of the present invention involves incising a sclerotomy in the eye transconjunctivally, with the surgical blade, through the pars plana and posterior to the limbus. Alternatively, the incision can be through another portion of the eye such as the anterior segment. The linear actuator is actuated sufficiently to reciprocate the cutting edge of the inner cutter across the aperture to cut a portion of vitreous extending into the aperture. The method involves aspirating the cut sample of vitreous through the longitudinal bore to a sample container. The method also involves injecting air, saline or similar fluid through the longitudinal bore and into the eye and removing the surgical blade from the eye. The operation is conducted through an incision small enough so as not to require sutures after the operation has been performed.

BRIEF DESCRIPTION OF THE DRAWINGS

FIG. 3a is an enlarged bottom plan view of the blade, inner cutter and outer cutter of the guillotine cutter of FIG. 1;

FIG. 3b is an enlarged side elevation of the blade, inner cutter and outer cutter of FIG. 3a;

FIG. 4a is an enlarged bottom plan view of an alternative stiletto tip which may be used with the guillotine cutter of FIG. 1;

FIG. 4b is an enlarged side elevation of the alternative stiletto tip of FIG. 4a;

FIG. 5a is an enlarged bottom plan view of an alternative broadhead tip which may be used with the guillotine cutter of FIG. 1;

FIG. 5b is an enlarged side elevation of the alternative broadhead tip of FIG. 5a; and FIG. 5c is an enlarged top elevation of the alternative broadhead tip of FIG. 5a.

DETAILED DESCRIPTION OF THE PREFERRED EMBODIMENT

Figure 1:
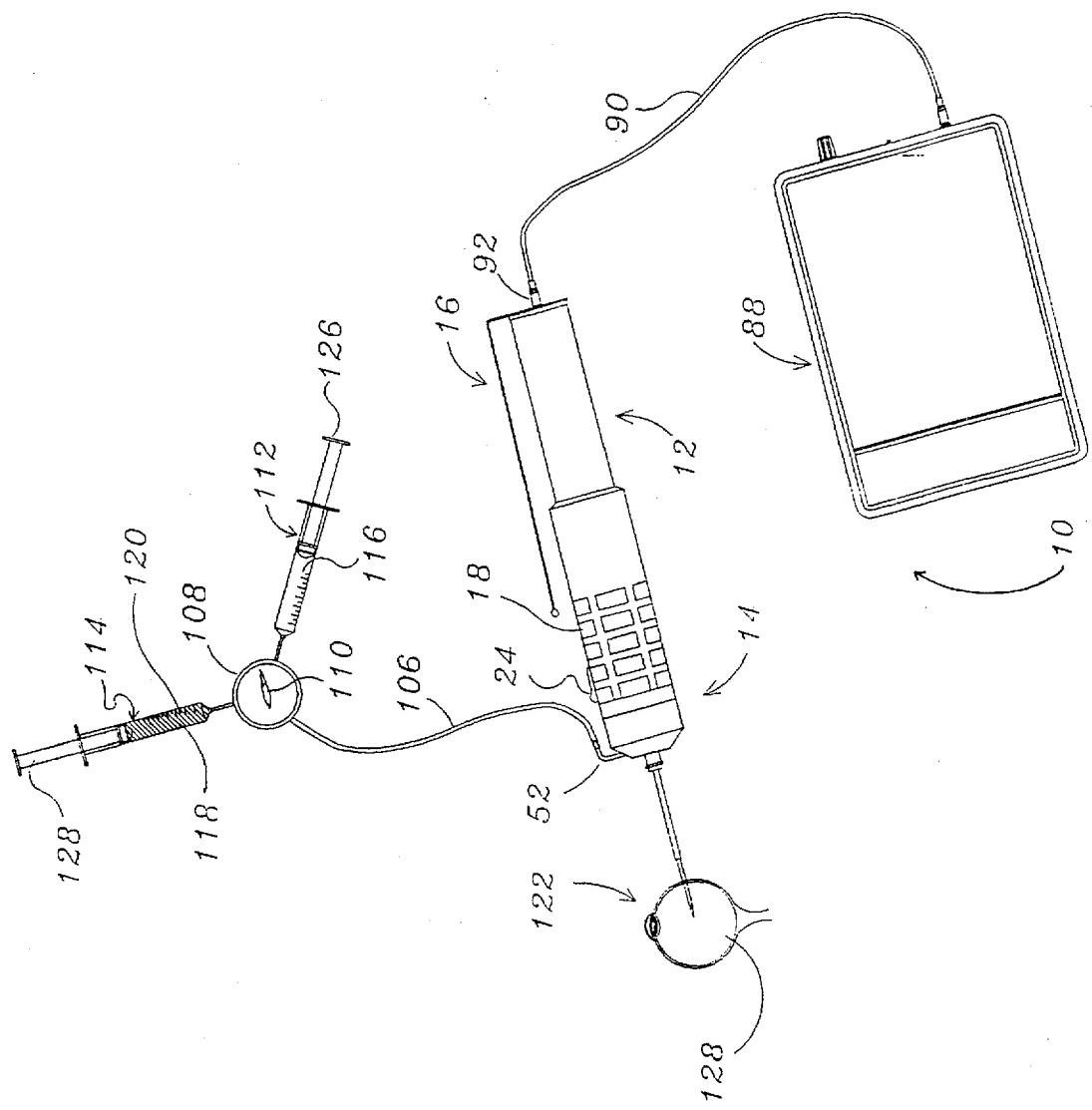
FIG. 1 is a side elevation of the guillotine cutter of the present invention shown with the cutting assembly positioned within an eye.
Figure 2:
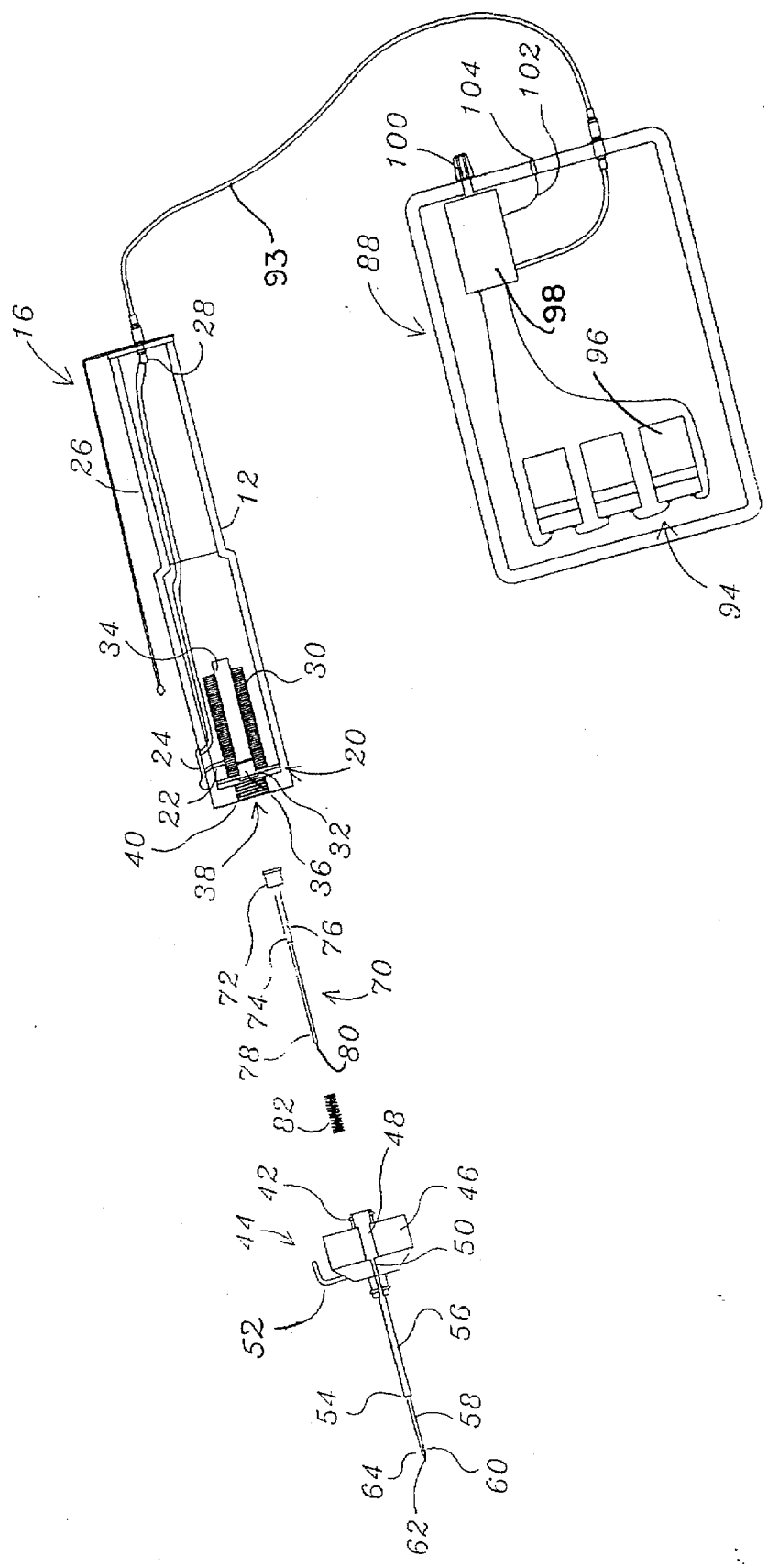
FIG. 2 is a partial exploded side elevation in cross-section showing the guillotine cutter of FIG. 1.

With reference to the drawings, shown in FIG. 1 is a guillotine cutter 10 having a housing 12 with a proximal end 14 and a distal end 16. The housing 12 is preferably provided with a plurality of studs 18 as shown in FIG. 1 or a similar non-stick surface to prevent slippage of the guillotine cutter 10 from the hand of a user (not shown). As shown in FIG. 2, positioned within the housing 12 is a linear actuator, which, in the preferred embodiment is a solenoid 20. The solenoid 20 is operably coupled by wires 22 to a switch 24 slidably received on the housing 12. The switch 24, in turn, is coupled via a set of wires 26 to a plug jack 28 provided on the distal end 16 of the housing 12.

The solenoid 20 includes an outer wire coil 30 defining a bore 32 in which slides an iron core 34. Secured to one end of the iron core 34 is a solenoid pusher 36 which may be constructed of tin, a steel manganese nickel alloy or e similar non-magnetic material. The solenoid 20 is secured within the housing 12 in such a manner that the solenoid pusher 36 may reciprocate into and out of a bore 38 provided in the proximal end 14 of the housing 12. As shown in FIG. 2, the bore 38 is provided with threads 40 for mating engagement with threads 42 provided on an outer cutter assembly 44. The outer cutter assembly 44 includes an anodized aluminum cap 46 provided with a throughbore 48. The throughbore 48 narrows to a smaller shaft 50 which is in communication with a fluid port 52 secured to the exterior of the cutter assembly 44. Extending from the end of the cap 46 is the outer cutter 54. The outer cutter 54 is constructed of twenty gauge stainless steel tubing 56 which narrows to twenty-three gauge stainless steel tubing 58 approximately eighteen millimeters from the end of the cap 46. The twenty-three gauge stainless steel tubing 58 extends an additional twelve millimeters beyond the end of the twenty gauge stainless steel tubing 56. Near the end of the twenty-three gauge stainless steel tubing 58 is an aperture 60 0.50 millimeters in diameter. The edges of this aperture 60 are beveled or sharpened to provide a cutting edge along the edge of the aperture 60. Connected to the end of the twenty-three gauge stainless steel tubing 58 is a surgical blade 62 secured to the twenty-three gauge stainless steel tubing by silver solder 64 or a similar securement method. As shown in FIGS. 3a and 3b, the surgical blade 62 is generally flat with a beveled cutting edge 66 which tapers to a point 68 and which may be diamond coated.

As shown in FIG. 2, the cutter 10 is also provided with an inner cutter 70 having a cutter pusher 72 secured to a length of twenty-three gauge stainless steel tubing 74 extending twelve millimeters beyond the cutter pusher 72. The twenty-three gauge stainless steel tubing 74 is provided with an aperture 76 one and one-tenth millimeters in diameter. The twenty-three gauge stainless steel tubing 74 is secured to a length of twenty-seven gauge stainless steel tubing 78 extending thirty-three millimeters beyond the end of the twenty-three gauge stainless steel tubing 74. The end of the twenty-seven gauge stainless steel tubing 78 is provided with a sharpened cutting edge 80. Provided around the inner cutter 70 is a return spring 82 which fits within the throughbore 48. As shown in FIGS. 2, 3a and 3b, when the inner cutter 70 is placed within the outer cutter assembly 44, the sharpened cutting edge 80 of the inner cutter 70 is capable of movement back and forth across the aperture 60 of the twenty-three gauge stainless steel tubing 58.

Alternatively, instead of the surgical blade 62 as shown in FIGS. 3a and 3b, the cutter may be provided with a stiletto tip 84 as shown in FIGS. 4a and 4b or a broad-head tip 86 as shown in FIGS. 5a, 5b and 5c. The twenty-three gauge stainless steel tubing 58 is designed small enough so that no sutures are required to repair an incision made by the surgical blade 62 secured to the twenty-three gauge stainless steel tubing 58. The dimensions of the inner cutter 70 are dictated by the dimensions of the outer cutter assembly 44. The inner cutter 70 is provided with dimensions designed to move close enough against the outer cutter 54 to shear material protruding through the cutting aperture 60 into the outer cutter 54. The inner cutter 70 is also small enough so as to not to generate undue friction as it moves across the interior of the outer cutter 54.

As shown in FIGS. 1 and 2, a power supply pack 88 is coupled to the distal end 16 of the housing 12 via a power transfer cable 90. The power transfer cable 90 is provided on one end with a plug 92 for releasable coupling into the plug jack 28 provided in the distal end 16 of the housing 12. As shown in FIG. 2, the power supply pack 88 is provided with a power source 94 which, in the preferred embodiment, is three nine-volt batteries 96. Also provided within the power supply pack 88 is a variable speed solenoid actuator 98 such as any type well known in the art. The solenoid actuator 98 is provided with an adjustment knob 100 mounted on the exterior of the power supply pack 88. Coupled to the solenoid actuator 98 by a set of wires 102 is a light emitting diode 104 which serves as a battery power indicator.

Coupled to the fluid port 52 is a transfer tube 106 as shown in FIG. 1. The transfer tube 106 is connected to a three-way stopcock 108. The three-way stopcock 108 is provided with a valve 110 which determines what material flows through the transfer tube 106 and in what direction. Secured to the three-way stopcock 108 is an aspiration syringe 112 and an irrigation syringe 114. The aspiration syringe 112 is provided with a sample chamber 116, while the irrigation syringe 114 is provided with a fluid chamber 118. In the preferred embodiment the fluid chamber 118 is provided with saline 120, but may, of course be provided with air or a similar fluid.

To use the guillotine cutter 10 of the present invention, a patient (not shown) is placed in a supine or sitting position and an eye 122 of the patient is prepared for surgery (FIG. 1). Anesthetic may be administered retrobulbar, peribulbar or sub-conjunctival. Preferably, a portable microscope, or slit lamp and indirect ophthalmoscopy (not shown) is used to view the operation. A lid speculum (not shown) such as those well-known in the art is inserted into the eye 122. The guillotine cutter 10 is then used to place an incision 124 transconjunctivally through the pars plana approximately 3.5 millimeters posterior to the limbus or through the anterior segment (FIG. 1).

The switch 24 is used to actuate the cutter 10 (FIGS. 1 and 2). Once the switch 24 has been actuated, the solenoid actuator 98 alternately draws the iron core 34 into the bore 32 and releases the iron core 34. As the iron core 34 is drawn into the bore 32, the solenoid pusher 36 is moved out of the bore 32 into the cutter pusher 72. As the cutter pusher 72 is driven by the solenoid 20, the cutting edge 80 of the inner cutter 70 moves across the aperture 60 provided in the twenty-three gauge stainless steel tubing 58. As the solenoid actuator 98 releases the iron core 34, the spring 82 drives the cutter pusher 72 toward the solenoid 20. The cutter pusher 72, in turn, forces the solenoid pusher 36 into the iron core 34 and the iron core 34 partially out of the bore 32. The solenoid actuator 98 may be adjusted with the adjustment knob 100 to cycle the inner cutter 70 at the appropriate speed. In the preferred embodiment the solenoid actuator 98 is capable of adjusting the cutting speed of the guillotine cutter 10 from between sixty to three hundred cycles per minute. The adjustment knob 100 of the solenoid actuator 98 is typically adjusted to achieve a cutter speed of about one hundred cycles per minute. The three-way stopcock 110 is positioned as shown in FIG. 1 and a plunger 126 of the aspiration syringe 112 is pulled back to draw vitreous 128 into the cutting aperture 60 (FIGS. 1 and 3a). As the cutting edge 80 of the inner cutter 70 moves across the cutting aperture 60, a portion of vitreous 128 is sliced off. As the plunger 126 of the aspiration syringe 112 is pulled back, the severed portion of vitreous 128 is drawn through the inner cutter 70 and out of the aperture 76. The vitreous 128 is drawn through the fluid port 52 and transfer tube 106 into the sample chamber 116 of the aspiration syringe 112. This continues until an appropriate amount of vitreous 128 has been drawn into the sample chamber 116.

Once the appropriate amount of vitreous 128 has been collected, the three-way stopcock 108 adjusted to allow the saline 120 to be injected from the irrigation syringe 114, through the transfer tube 106 and into the eye 122. As a plunger 128 of the irrigation syringe 114 is depressed the saline 120 flows through the three-way stopcock 108 through the transfer tube 106 and through the fluid port 52. The saline 120 moves through the aperture 76 of the inner cutter 70 and through the inner cutter 70. The saline 120 moves out of the inner cutter 70 and through the cutting aperture 60 into the eye 122. Once an appropriate amount of saline 120 has been injected into the eye 122, the guillotine cutter 10 is removed from the eye 122.

The guillotine cutter 10 is preferably removed from the eye 122 with the cutting edge 80 of the inner cutter 70 not covering the cutting aperture 60 so as to prevent torsional damage to the vitreous 128 from being caught between the cutting edge 80 of the inner cutter 70 and the cutting aperture 60. Due to the small gauge of the twenty-three gauge stainless steel tubing 58, the incision 124 is small enough that no sutures are required for the eye 122 to heal.

After the operation, distilled water (not shown) or a similar cleansing agent is forced through the transfer tube 106 and out the cutting aperture 60. The cleansing agent is then forced through the cutting aperture 60 and out the transfer tube 106 to clear the guillotine cutter 10 of any remaining vitreous 128 or other debris. Once the guillotine cutter 10 has been cleansed, the plug 92 and a power cord 93 attached thereto are removed from the plug jack 28. The outer cutter assembly 44 is unscrewed from the housing 12 and the power cord 93, outer cutter assembly 44, inner cutter 70, fluid transfer tube 106, spring 82 and housing 12 may be sterilized by ethylene oxide or steam autoclave according to recognized standards and recommended practices. Preferably, however, only the housing 12 and power cord 93 are sterilized, while the outer cutter assembly 44, inner cutter 70, fluid transfer tube 106 and spring 82 are discarded. A new, sterilized outer cutter assembly 44, inner cutter 70, fluid transfer tube 106 and spring 82 are then assembled on the housing 12 as described above and the guillotine cutter 10 is thereafter again ready for use.

Although the invention has been described with respect to a preferred embodiment thereof, it is to be understood that it is not to be so limited, since changes and modifications can be made therein which are within the full intended scope of this invention as defined by the appended claims. For example, it is anticipated that various styles of tips may be secured to the stainless steel twenty-three gauge tubing 58 to make various types of incisions in the eye 122 of a patient. Additionally, it is anticipated that various types and dimensions of blades and cutters may be used to perform the sutureless vitrectomy described above. It is also anticipated that the cutter may be mechanically, electrically or pneumatically actuated.

What is claimed is:

1. An intraocular surgical tool for removing material from an eye of a patient comprising:
   (a) a housing having a proximal end and a distal end;
   (b) an outer cutter coupled to said proximal end of said housing, said outer cutter having a distal end and a sidewall defining a longitudinal bore, said sidewall being provided with an aperture;
   (c) means secured distally of said outer cutter for incising the eye; said incising means projecting distally from said distal end of said outer cutter to a tapered distal tip;
   (d) an inner cutter having a cutting edge telescopically received in said longitudinal bore of said outer cutter and adapted for travel of said cutting edge across said aperture;
   (e) a linear actuator provided within said housing and drivably coupled to said inner cutter; and
   (f) means releasably coupled to said linear actuator for powering said linear actuator.

2. The intraocular surgical tool of claim 1, wherein said incising means is a surgical blade.

3. The intraocular surgical tool of claim 2, wherein said surgical blade is of a size sufficient to make an incision which is small enough to heal without sutures and wherein said incision is large enough to allow insertion of said outer cutter through said incision.

4. The intraocular surgical tool of claim 1, wherein said outer cutter is no larger than twenty-three gauge.

5. The intraocular surgical tool of claim 1, wherein said powering means is a power source chosen from the group consisting of mechanical, electrical and pneumatical.

6. The intraocular surgical tool of claim 1, further comprising means operably coupled to said powering means for varying a cycling speed of said linear actuator.

7. The intraocular surgical tool of claim 6, wherein said varying means is a solenoid actuator capable of varying cycling of said linear actuator from at least between about seventy-five to about one hundred seventy-five cycles per minute.

8. The intraocular surgical tool of claim 1, further comprising means operably coupled to said housing for stopping and starting said linear actuator.

9. The intraocular surgical tool of claim 1, wherein said housing is constructed of a material which is not damaged by ethylene oxide sterilization.

10. The intraocular surgical tool of claim 1, wherein said housing is constructed of a material which is not damaged by steam autoclave sterilization.

11. The intraocular surgical tool of claim 1, wherein said outer cutter, said incising means and said inner cutter are disposable.

12. The intraocular surgical tool of claim 1, further comprising suctioning means in operable communication with said longitudinal bore for applying a suction to said longitudinal bore.

13. The intraocular surgical tool of claim 12, wherein said suctioning means is a suction tube provided in operable communication with said longitudinal bore.

14. The intraocular surgical tool of claim 1, further comprising means for injecting fluid into said longitudinal bore.

15. The intraocular surgical tool of claim 14, wherein said injecting means is an injector in operable communication with said longitudinal bore.

16. The intraocular surgical tool of claim 15, further comprising a three-way stopcock in operable communication with said longitudinal bore, said suction tube, and said injecting means.

17. An intraocular surgical tool for removing material from an eye of a patient comprising:
   (a) a housing having a proximal end and a distal end;
   (b) a disposable outer cutter having a sidewall defining a longitudinal bore, said sidewall being provided with an aperture;
   (c) disposable means secured to said outer cutter for incising the eye;
   (d) a disposable inner cutter having a cutting edge telescopically received in said longitudinal bore of said outer cutter and adapted for travel of said cutting edge across said aperture;
   (e) a linear actuator provided within said housing and driveably coupled to said inner cutter;
   (f) means releasably coupled to said linear actuator for powering said linear actuator;
   (g) means operably coupled to said powering means for varying cycling of said linear actuator;
   (h) a tube in operable communication with said longitudinal bore;
   (i) a three-way stopcock operably coupled to said tube;
   (j) suctioning means coupled to said three-way stopcock for applying a suction to said tube; and
   (k) injecting means operably coupled to said three-way stopcock for injecting fluid into said tube.

18. A method for performing a vitrectory for removing a portion of vitreous from an eye comprising:
   (a) providing an intraocular surgical tool for removing material from an eye of a patient comprising:
      (i) a housing having a proximal end and a distal end;
      (ii) an outer cutter having a sidewall defining a longitudinal bore, said sidewall being provided with an aperture;
      (iii) means secured distally of said outer cutter for incising the eye; said incising means projecting distally from said distal end of said outer cutter to a tapered distal tip;
      (iv) an inner cutter having a cutting edge telescopically received in said longitudinal bore of said outer cutter and adapted for travel of said cutting edge across said aperture;
      (v) a linear actuator provided within said housing and operably coupled to said inner cutter; and
      (vi) means releasably coupled to said linear actuator for powering said linear actuator;
   (b) incising a sclerotomy in the eye with said incising means transconjunctivally through the pars plana;
   (c) cutting a sample of vitreous from the eye;
   (d) aspirating said sample of vitreous through said longitudinal bore to a sample container; and
   (e) removing said incising means from the eye.

19. The method of claim 18, further comprising allowing the eye to heal without sutures.

20. The method of claim 18, wherein said intraocular surgical tool makes an incision in the eye less than 0.60 millimeters in diameter.

21. The method of claim 18, further comprising injecting a fluid through said longitudinal bore and into the eye.

* * * * *